US00PP28423P2

(12) United States Plant Patent
Hanes

(10) Patent No.: US PP28,423 P2
(45) Date of Patent: Sep. 19, 2017

(54) ***PELARGONIUM* PLANT NAMED 'PEQZ0008'**

(50) Latin Name: *Pelargonium interspecific*
Varietal Denomination: PEQZ0008

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,662

(22) Filed: Jun. 9, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

(56) References Cited

PUBLICATIONS

PLUTO Plant Variety Database p. 1 2017.*

* cited by examiner

*Primary Examiner* — Annette Para
(74) *Attorney, Agent, or Firm* — Dale Skalla

(57) ABSTRACT

A new *Pelargonium* plant named 'PEQZ0008' particularly distinguished by the coral salmon single petal inflorescences held above the dark green foliage. The variety is very heat and drought tolerant with continuous color through the most extreme summer heat, and exceptional edema tolerance on a well-branched plant habit.

2 Drawing Sheets

Latin name of the genus and species of the plant claimed: *Pelargonium interspecific.*
Varietal denomination: 'PEQZ0008'.

BACKGROUND OF THE NEW PLANT

The present invention comprises a new *Pelargonium*, botanically known as *Pelargonium interspecific*, and hereinafter referred to by the variety name 'PEQZ0008'.

'PEQZ0008' is a product of a planned breeding program. The new cultivar 'PEQZ0008' has an intense coral salmon single flower form held above the dark green foliage. It is very heat and drought tolerant with continuous color through the summer heat and has a trailing habit that is good in ground beds or hanging baskets.

'PEQZ0008' originates from a hybridization in a controlled breeding program made in May 2007 in a greenhouse in Gilroy, Calif. The female parent was an unpatented, proprietary plant of *P. interspecific* parentage, identified as '10520-1' with dark foliage and more open plant habit when compared to 'PEQZ0008'.

The male parent of 'PEQZ0008' was an unpatented, proprietary plant of *P. interspecific* parentage, identified as '10436-1' with lavender pink colored florets and trailing plant habit when compared to 'PEQZ0008'. The resultant seed was sown in February 2008.

'PEQZ0008' was selected as one flowering plant within the progeny of the stated cross in May 2008 in a greenhouse in Gilroy, Calif.

The first act of asexual reproduction of 'PEQZ0008' was accomplished when vegetative cuttings were propagated from the initial selection in the July 2008 in a greenhouse in Gilroy, Calif.

BRIEF SUMMARY OF INVENTION

Horticultural examination of plants grown from cuttings of the plant initiated in Jun. 7, 2016 in Gilroy, Calif., and continuing thereafter, has demonstrated that the combination of characteristics as herein disclosed for 'PEQZ0008' are firmly fixed and are retained through successive generations of asexual reproduction.

'PEQZ0008' has not been observed under all possible environmental conditions. The phenotype may vary significantly with variations in environment such as temperature, light intensity, and day length.

A Plant Breeder's Right for this cultivar was applied for in the European Union on Jun. 10, 2015, No. 2015/1214. 'PEQZ0008' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
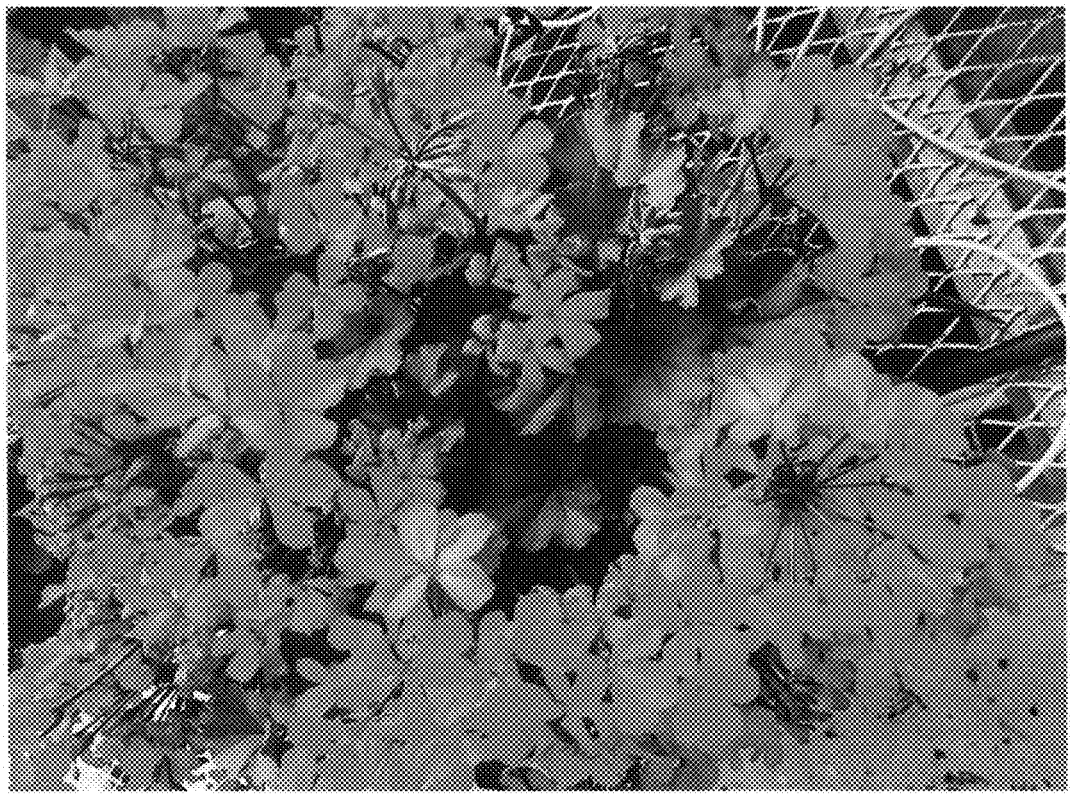
Figure 2:
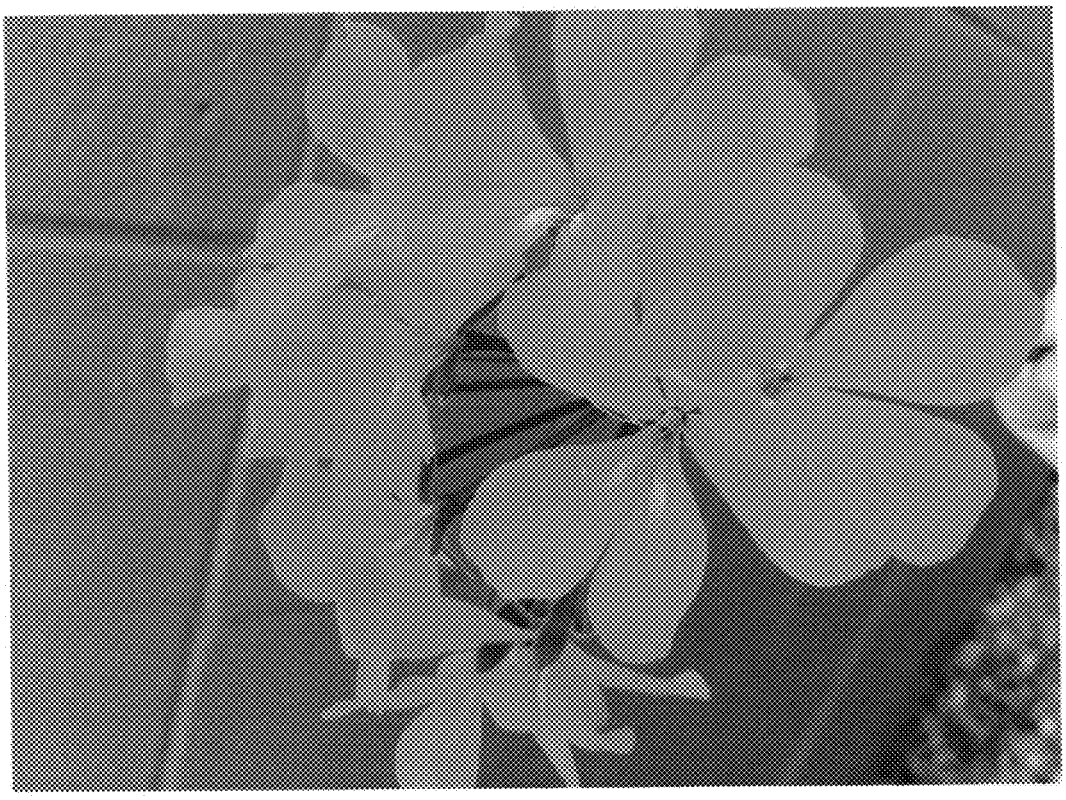

The accompanying photographic drawings show typical flower and foliage characteristics of 'PEQZ0008' with colors being as true as possible with an illustration of this type. The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. on Jun. 7, 2016 under natural light. These plants were approximately 7 weeks old and were grown in a 4 cell packs in a greenhouse trial.

Color references are made to The Royal Horticultural Society Colour Chart (R.H.S.) 2001.

Plant:

*Form, growth and habit.*—Upright and outwardly spreading growth on a dark leaf well-branched plant that is, heat and drought tolerant. It is with continuous color through the most extreme summer heat, and is edema tolerance.

*Plant height.*—10 cm.

*Plant height (inflorescence included).*—16 cm.

*Plant width.*—15 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS 156B.

Foliage:

*Immature leaf, color upper surface.*—RHS 137C.

*Immature leaf, lower surface.*—RHS 137D.

*Mature leaf, color upper surface.*—RHS 147A.

*Mature leaf, color lower surface.*—RHS 147B.

*Length.*—4.2-4.4 cm.

*Width.*—6.8-7.0 cm.

*Shape.*—Reniform.

*Base shape.*—Reniform.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137A.

*Color of veins, lower surface.*—RHS 137A.

*Pattern of veining.*—Palmate.

*Petiole color.*—RHS N199A.

*Petiole length.*—6.5-7.0 cm.

*Diameter of petiole.*—0.3 cm.

*Texture.*—Pilose, hirsute, glandular hairs.

Stem:

*Quantity of branches.*—4-5.

*Color of stem.*—RHS 183A.

*Length of stem.*—6.5 cm.

*Diameter.*—0.6 cm.

*Length of internodes.*—1.2 cm.

*Texture.*—Sparsely hirsute, pilose, glandular hairs.

Peduncle:

*Color of peduncle.*—RHS 200.

*Length of peduncle.*—10 cm.

*Peduncle diameter.*—0.3 cm.

*Texture.*—Hirsute, glandular hairs.

Pedicel:

*Color of pedicel.*—RHS 183A.

*Length of pedicel.*—3.2-3.5 cm.

*Diameter of pedicel.*—0.2 cm.

*Texture.*—Sparsely pilose, glandular hiars.

Bud (just before opening):

*Color.*—RHS 41A.

*Length.*—1.6 cm.

*Width.*—0.6-0.7 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12, with 15 immature umbels in various stages.

*Fragrance.*—None.

*Umbel diameter.*—11 cm.

*Umbel depth.*—5.8-6.0 cm.

Corolla:

*Form.*—Single.

*Number of petals.*—5.

*Diameter of flower.*—4.5-4.8 cm.

*Depth of flower.*—0.8-1.0 cm.

*Color upper petals, upper surface.*—RHS N57B.

*Color upper petals, lower surface.*—RHS 58C.

*Length of upper petals.*—2.7 cm.

*Width of upper petals.*—1.7 cm.

*Color lower petals, upper surface.*—RHS 51A.

*Color lower petals, lower surface.*—RHS 52B.

*Length of lower petals.*—2.5 cm.

*Width of lower petals.*—1.3 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 146B.

*Length of sepals.*—1.2 cm.

*Width of sepals.*—0.4-0.5 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.9 cm.

*Style color.*—RHS 53D.

*Style length.*—0.5-0.6 cm.

*Stigma color.*—RHS 53D.

*Ovary color.*—RHS N155B.

*Ovary length.*—0.5-0.6 cm.

*Ovary diameter.*—0.3 cm.

Androecium:

*Number of stamens.*—7-8.

*Color of filaments.*—RHS N57B with RHS N155C.

*Length filaments.*—0.6 cm.

*Anther color.*—RHS 48A.

*Length of anthers.*—0.2 cm.

*Color of pollen.*—RHS 25B.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0008' substantially as illustrated and described herein.

* * * * *